(12) United States Patent
Rohl et al.

(10) Patent No.: US 11,065,121 B2
(45) Date of Patent: Jul. 20, 2021

(54) INTRODUCER SYSTEMS, DEVICES AND METHODS FOR HEART VALVE REDUCTIONS

(71) Applicants: BOSTON SCIENTIFIC SCIMED, INC., Maple Grove, MN (US); MAYO FOUNDATION FOR MEDICAL EDUCATION AND RESEARCH, Rochester, MN (US)

(72) Inventors: James P. Rohl, Prescott, WI (US); David J. Lehse, Oakdale, MN (US); Devon N. Arnholt, Shoreview, MN (US); Benn Horrisberger, Blaine, MN (US); Joel T. Eggert, Plymouth, MN (US); Peter M. Pollak, Atlantic Beach, FL (US); Joseph A. Dearani, Rochester, MN (US); Katherine Lorraine Baldwin, Minneapolis, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 434 days.

(21) Appl. No.: 16/313,458

(22) PCT Filed: Dec. 16, 2016

(86) PCT No.: PCT/US2016/067285
§ 371 (c)(1),
(2) Date: Dec. 26, 2018

(87) PCT Pub. No.: WO2017/106720
PCT Pub. Date: Jun. 22, 2017

(65) Prior Publication Data
US 2019/0142591 A1      May 16, 2019

Related U.S. Application Data

(60) Provisional application No. 62/269,497, filed on Dec. 18, 2015.

(51) Int. Cl.
*A61F 2/24* (2006.01)
*A61B 90/00* (2016.01)
(Continued)

(52) U.S. Cl.
CPC ........ *A61F 2/2466* (2013.01); *A61B 1/00082* (2013.01); *A61B 1/00098* (2013.01);
(Continued)

(58) Field of Classification Search
CPC .......... A61B 17/00; A61B 1/00; A61B 90/00; A61B 1/00082; A61B 90/361;
(Continued)

(56) References Cited

U.S. PATENT DOCUMENTS 6,338,717 B1    1/2002  Ouchi
2004/0039371 A1  2/2004  Tockman et al.
(Continued)

FOREIGN PATENT DOCUMENTS

JP    2000185042 A    7/2000
JP    2005536262 A    12/2005
(Continued)

OTHER PUBLICATIONS

International Search Report and Written Opinion dated May 18, 2017 for International Application No. PCT/US2016/067285.
(Continued)

*Primary Examiner* — George J Ulsh
(74) *Attorney, Agent, or Firm* — Seager, Tufte & Wickhem, LLP

(57) ABSTRACT

An introducer catheter device comprising a handle and an elongate shaft coupled to the handle and extending therefrom. The shaft defines a lumen therethrough, a longitudinal axis, and a first aperture in connection with the lumen. The shaft includes a movable deployment element configured for
(Continued)

deploying an ancillary device from the first aperture at an angle relative to the longitudinal axis.

12 Claims, 15 Drawing Sheets

(51) Int. Cl.
| | |
|---|---|
| *A61B 1/00* | (2006.01) |
| *A61B 1/05* | (2006.01) |
| *A61M 25/00* | (2006.01) |
| *A61M 25/01* | (2006.01) |
| *A61B 17/04* | (2006.01) |
| *A61B 17/128* | (2006.01) |
| *A61B 17/00* | (2006.01) |

(52) U.S. Cl.
CPC .............. *A61B 1/05* (2013.01); *A61B 90/361* (2016.02); *A61M 25/0082* (2013.01); *A61M 25/0136* (2013.01); *A61M 25/0147* (2013.01); *A61B 17/1285* (2013.01); *A61B 2017/00247* (2013.01); *A61B 2017/0409* (2013.01); *A61B 2017/0464* (2013.01); *A61F 2220/0008* (2013.01); *A61M 2025/0095* (2013.01); *A61M 2025/0096* (2013.01)

(58) Field of Classification Search
CPC ... A61B 1/00098; A61B 1/00133; A61B 1/05; A61B 2017/00247; A61B 2017/0409; A61B 2017/0464; A61B 17/1285; A61F 2/2466; A61F 2220/0008; A61M 25/0082; A61M 25/0136; A61M 25/0147; A61M 2025/0095; A61M 2025/0096
See application file for complete search history.

(56) References Cited

U.S. PATENT DOCUMENTS

| | | | |
|---|---|---|---|
| 2007/0293719 A1* | 12/2007 | Scopton | ................ A61B 1/018 600/106 |
| 2010/0114114 A1 | 5/2010 | Tockman et al. | |
| 2016/0045098 A1 | 2/2016 | Tsubouchi | |

FOREIGN PATENT DOCUMENTS

| | | |
|---|---|---|
| JP | 2006527629 A | 12/2006 |
| JP | 2015516859 A | 6/2015 |
| WO | 2004030718 A2 | 10/2004 |
| WO | 2005002660 A1 | 1/2005 |
| WO | 2007149618 A2 | 12/2007 |
| WO | 2013159066 A1 | 10/2013 |
| WO | 2014112101 A1 | 7/2014 |

OTHER PUBLICATIONS

International Preliminary Report on Patentability dated Jun. 28, 2018 for International Application No. PCT/US2016/067285.

* cited by examiner

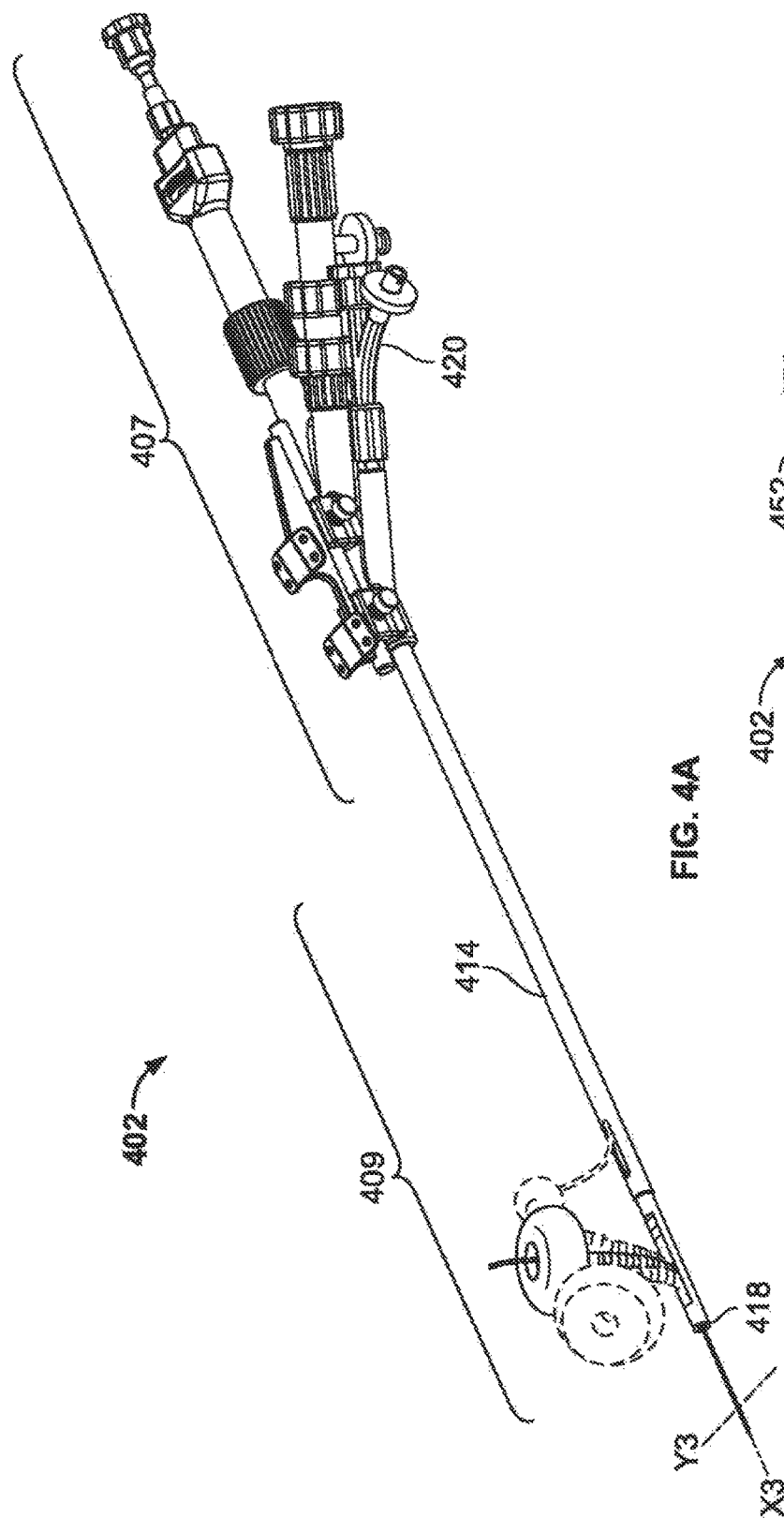
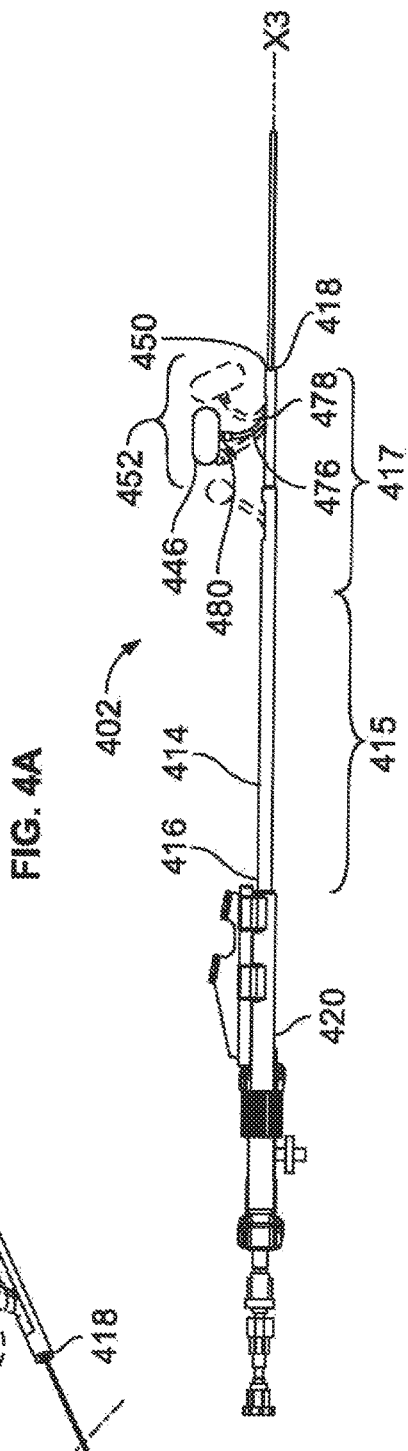
FIG. 4A
FIG. 4B

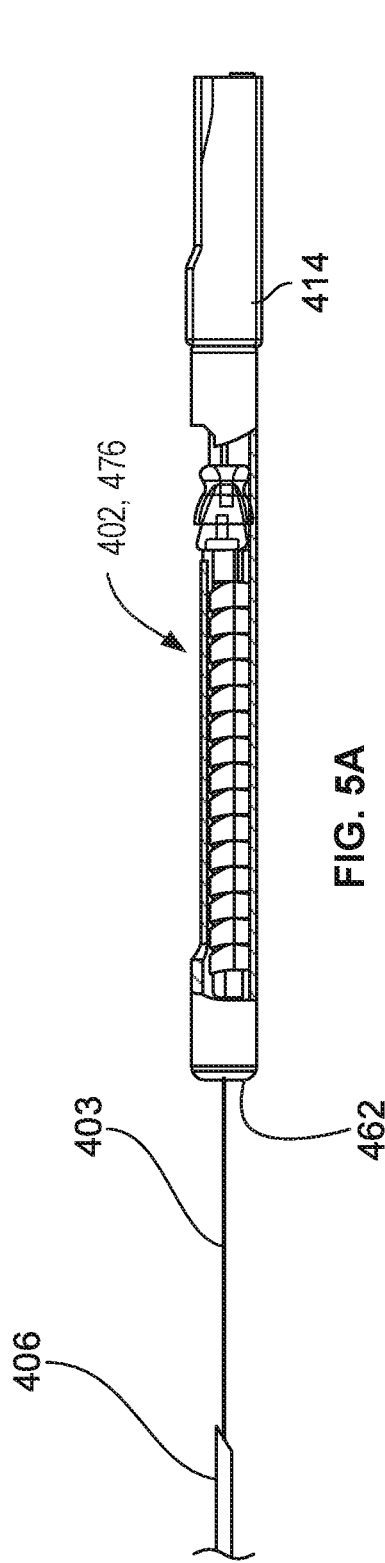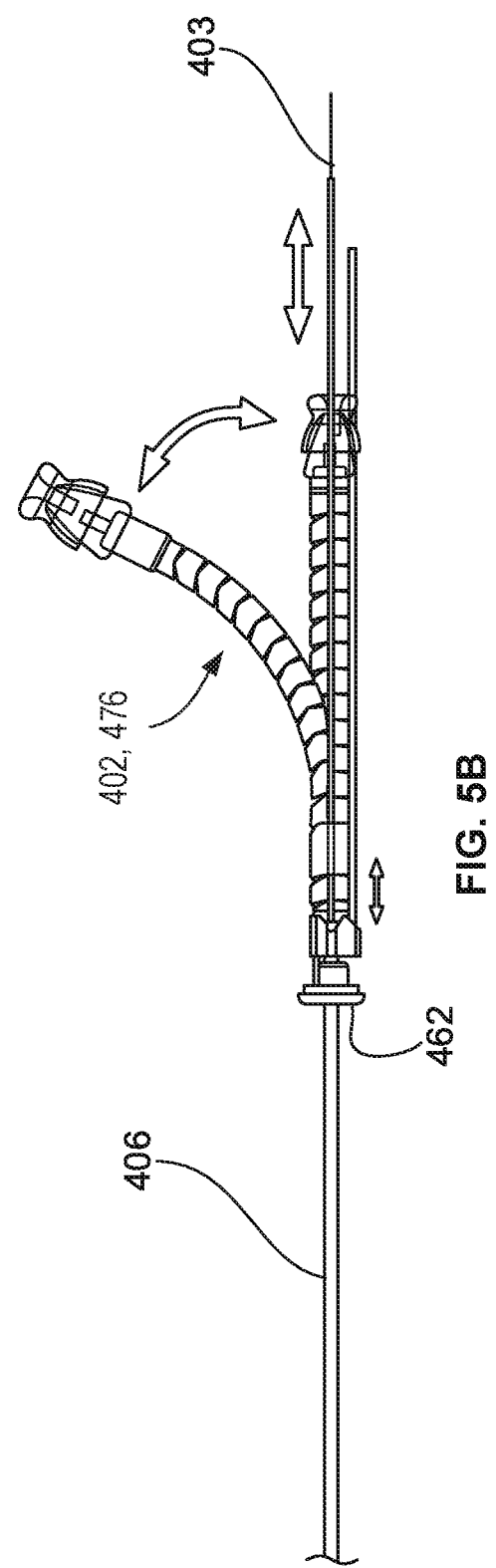

INTRODUCER SYSTEMS, DEVICES AND METHODS FOR HEART VALVE REDUCTIONS

CROSS-REFERENCE TO RELATED APPLICATIONS

This application is a National Stage of International Application No. PCT/US2016/067285, filed Dec. 16, 2016, which claims the benefit of priority under 35 U.S.C. § 119 to U.S. Provisional Application Ser. No. 62/269,497 filed Dec. 18, 2015, the entire disclosures of which are incorporated herein by reference.

TECHNICAL FIELD

The present invention relates to introducer systems, devices, and methods relating to heart valve reduction procedures.

BACKGROUND

A tricuspid valve is the valve located between a right atrium and a right ventricle in a mammalian heart. In a normally functioning tricuspid valve, when the valve is open, blood is allowed to be pumped from the right atrium into the right ventricle. When the valve is closed, blood is blocked from passing back from the right ventricle to the right atrium. However, when tricuspid regurgitation occurs, the tricuspid valve fails to open and close properly such that blood is allowed to flow backwards from the right ventricle to the right atrium of the heart. Tricuspid regurgitation can be treated by an annular reduction repair procedure that can be performed using a cardiac surgery procedure.

Current methods of tricuspid valve reduction surgery involves open heart surgery. The physician uses pledgets and sutures to plicate the tissue or, alternatively, uses a rigid or semi-rigid C-shaped ring to hold the valve tissue in place.

In a conventional cardiac heart valve replacement surgical procedure, the patient must typically be placed on cardio-pulmonary by-pass. During cardio-pulmonary by-pass, the flow of blood into and out of the heart and lungs is interrupted, and the blood flow is routed to a conventional blood pump and oxygenation unit. It is known that complications and side-effects are associated with cardiopulmonary by-pass, and it is generally believed that it is in the best interest of a patient to expedite the cardiac surgical procedure and remove the patent from cardio-pulmonary by-pass as quickly as possible. Complications and side effects associated with cardio-pulmonary surgery typically include the generation of emboli, hemolysis and degradation of the blood's oxygen carrying capacity, and inflammatory response in the blood. Some or all of these complications may be caused contact with the components of the cardio-pulmonary bypass equipment. The severity and incidence of potential side effects may be related to the length of the period of time that the patient is being supported on cardio-pulmonary by-pass.

Accordingly, there is a need for devices and methods for performing tricuspid regurgitation repair using minimally invasive catheter based procedures to reduce patient recovery time and health risks.

SUMMARY

Disclosed herein are various embodiments of tricuspid annulus reduction introducer systems, devices, and methods.

In Example 1, an introducer catheter device includes a handle and an elongate shaft coupled to the handle and extending therefrom. The shaft defines a lumen therethrough, a longitudinal axis, and a first aperture in connection with the lumen. The shaft includes a movable deployment element configured for deploying an ancillary device from the first aperture at an angle relative to the longitudinal axis.

In Example 2, the introducer catheter device of Example 1, wherein the deployment element includes a slidable member and a rail member, the slidable member is configured to slidably move along the rail member such that as the slidable member advances in a longitudinal direction either proximally or distally relative to the rail member, the slidable member articulates to a predetermined angle.

In Example 3, the introducer catheter device of Example 2, wherein the predetermined angle of the slidable member ranges from about 1 degree to about 180 degrees.

In Example 4, the introducer catheter device of Example 2 or Example 3, wherein the deployment element, when in a fully deployed state, is positioned at an angle ranging from about 60 degrees to about 80 degrees relative to a longitudinal axis defined by the shaft.

In Example 5, the introducer catheter device of any of Examples 2-4, wherein the deployment element is configured to actuate into a fully deployed state when the slidable member is advanced a predetermined distance in the longitudinal direction proximal to the rail member.

In Example 6, the introducer catheter device of Example 5, wherein the predetermined distance ranges from about 5 mm to about 10 mm.

In Example 7, the introducer catheter device of any of Examples 2-6, wherein the slidable member includes a distal face defining an opening, the opening being sized to engage with a portion of the ancillary device received therein.

In Example 8, the introducer catheter device of any of Examples 1-7, wherein the deployment element includes a deflectable shaft fully disposed within a cavity defined within the shaft when in a first configuration, and at least partially deflectable in a radially outward direction relative to the cavity in a second configuration.

In Example 9, the introducer catheter device of Example 8, further including an actuator coupled to the handle, and a cable coupled to and extending from the actuator to the deflectable shaft, wherein the actuator is configured to apply tension to the cable to deflect the deflectable shaft into the second configuration.

In Example 10, the introducer catheter device of Example 8 or Example 9, wherein the deflectable shaft deflects to a curve angle that ranges from about 45 degrees to about 180 degrees, or from about 30 degrees to about 270 degrees.

In Example 11, the introducer catheter device of any of Examples 1-10, wherein the shaft of the introducer catheter device includes a weeping balloon encapsulating a shaft portion including a digital camera.

In Example 12, a system including the introducer catheter device of Example 1 and a needle catheter device. The needle catheter device includes a proximal end, a distal end that includes a needle tip, and an elongate shaft configured for being received within the lumen of the introducer catheter device. At least a portion of the needle catheter device is extendable through the first aperture.

In Example 13, the system of any of Examples 1-12, wherein the shaft defines a second aperture in connection with the lumen, the second aperture including an elongate slot formed longitudinally along the shaft.

In Example 14, a system including the introducer catheter device of Example 1 and a visualization catheter including a proximal end, a distal end, and an elongate shaft therebetween, the distal end including a deployable weeping balloon, and the shaft being configured to be received within the lumen of the introducer catheter device and extendable through the second aperture of the shaft.

In Example 15, a method of reducing a heart valve includes inserting a first ancillary device into an introducer device assembly, introducing the introducer catheter assembly to a patient's vasculature, advancing the introducer catheter assembly through the vasculature to a heart such that the first aperture of the introducer catheter assembly is positioned within a heart chamber, and actuating the movable deployment element of the introducer catheter assembly such that the first ancillary device can be deployed from the first aperture of the introducer device at an angle relative to a longitudinal axis defined by an elongate shaft of the introducer assembly device. The introducer catheter assembly can include a handle and the elongate shaft coupled to the handle and extending therefrom. The shaft can define a lumen therethrough, the longitudinal axis, and a first aperture in connection with the lumen. The shaft further includes a movable deployment element configured for deploying a secondary device from the first aperture at an angle relative to the longitudinal axis.

In Example 16, the method of Example 15, wherein the first aperture of the introducer catheter assembly is positioned within a right atrium of the heart.

In Example 17, the method of Example 15 or Example 16, wherein the introducer device includes inflating a visualization balloon coupled to the shaft at the first aperture, or a location adjacent to the first aperture.

In Example 18, the method of any of Examples 15-17, wherein the first ancillary device is advanced through targeted tissue, the first ancillary device including a proximal end, a distal end, and an elongate shaft, where the distal end includes a needle tip and the shaft is configured for being received within the lumen of the introducer.

In Example 19, the method of any of Examples 15-18, wherein the first ancillary device delivers at least one tissue anchor configured to plicate targeted tissue.

In Example 20, the method of any of Examples 15-20, further including inserting a second ancillary device into the introducer device assembly, and advancing the second ancillary device through a second aperture of the introducer catheter assembly into the heart chamber, wherein the second ancillary device includes a visualization catheter including a proximal end, a distal end including a deployable weeping balloon, and an elongate shaft between the proximal and distal ends.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 1A shows the system inserted in a patient's body. FIG. 1B is a magnified view showing the system within the patient's heart, which is partially cross-sectioned to allow the system to visualized within the patient's right atrium.

FIG. 2A shows proximal and distal portions of the introducer catheter assembly. FIG. 2B shows a magnified view of a first distal portion of the introducer catheter assembly, in which a distal portion of a visualization catheter is shown extending therefrom. FIG. 2C shows a magnified view of a second distal portion of the introducer catheter assembly configured for introducing a needle catheter assembly into the patient's anatomy. FIG. 2D shows a magnified view of the first and second distal portions of the introducer catheter assembly and the visualization catheter assembly extending from the first distal portion.

FIGS. 3A and 3B are perspective views of the device shown in a fully assembled state and an exploded state, respectively. FIGS. 3C and 3D are plan views of the device showing the entire length of the device and a magnified view of a distal portion of the device, respectively. FIG. 3E is a magnified side view of a distal portion of the device.

FIGS. 4A-4E are views of another exemplary introducer catheter device provided herein. FIGS. 4A and 4C are perspective views of the device and FIG. 4B is a side view of the device. FIGS. 4D and 4E are magnified views of a distal portion of the device.

FIGS. 5A-5D are a series of illustrations showing how the exemplary introducer catheter device of FIGS. 4A-4E may be actuated as a system.

Figure 1A:
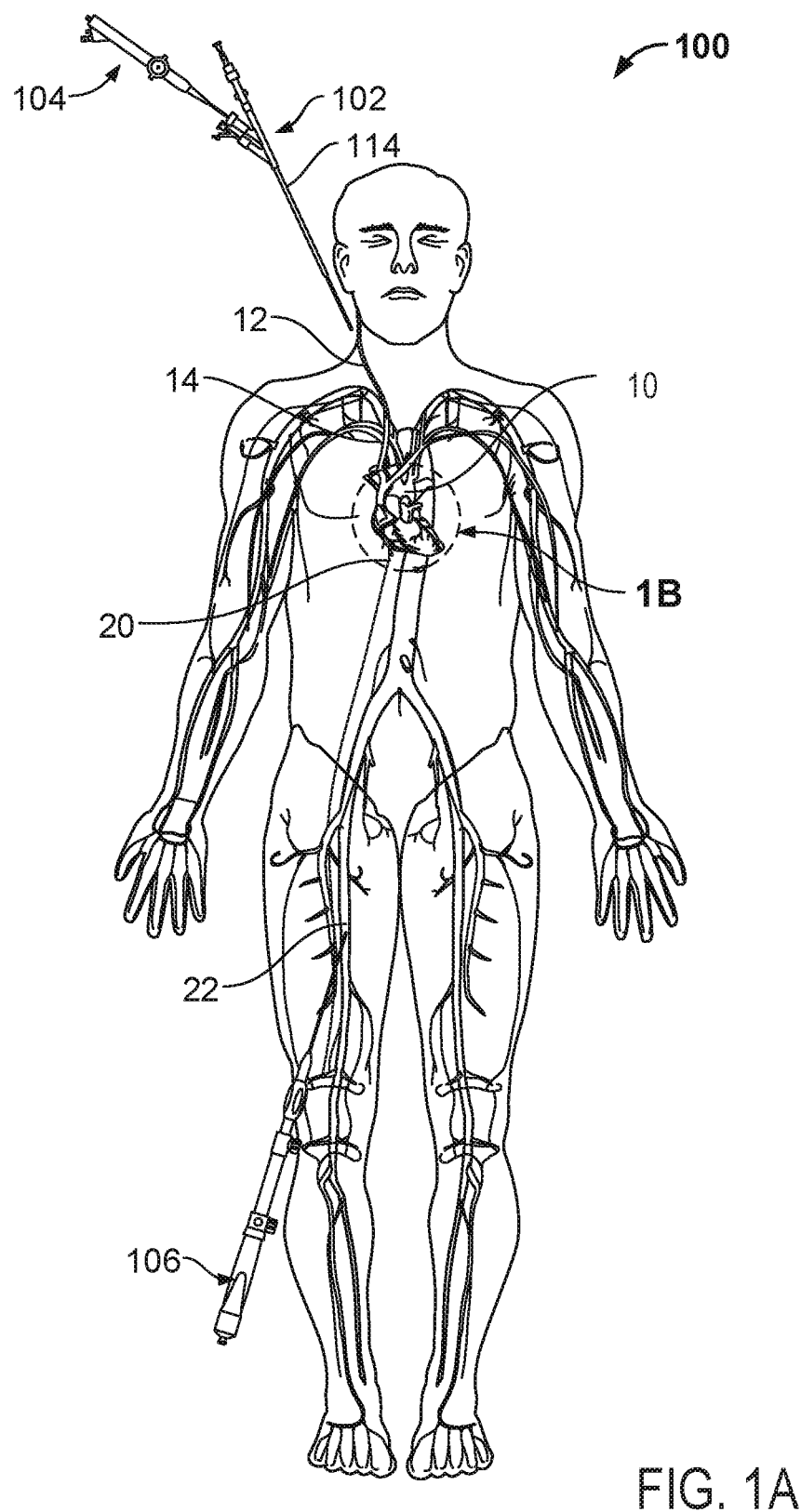
FIGS. 1A and 1B are illustrations of an exemplary system provided herein for performing an annulus reduction procedure on a tricuspid heart valve.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1B:
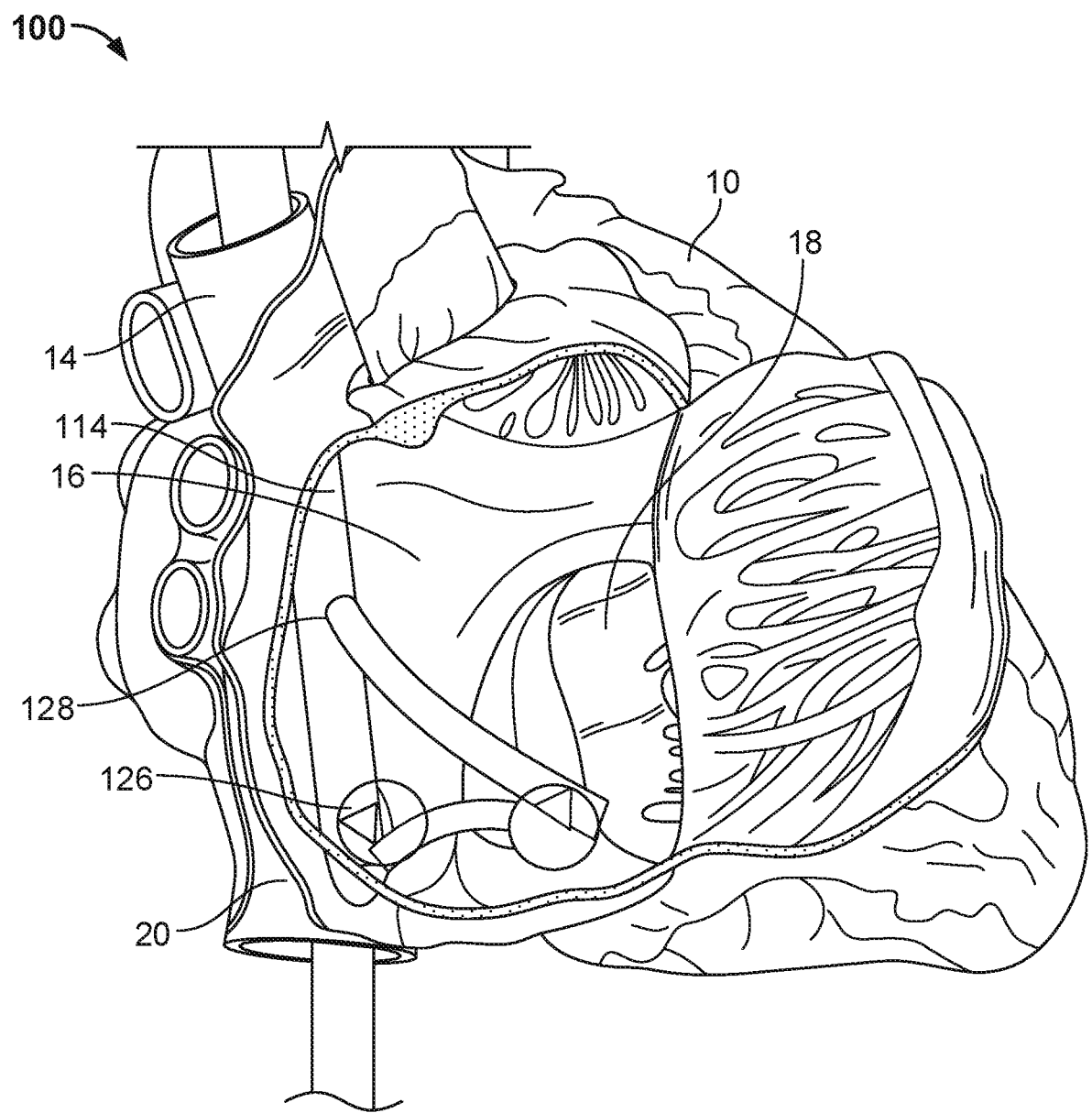

Referring to FIGS. 1A and 1B, an exemplary heart valve annulus reduction device system 100 includes an introducer catheter assembly 102, a visualization catheter assembly 104, and a needle catheter assembly 106 for performing an annulus reduction procedure on a heart 10. For example, the system 100 can be used to perform an annulus reduction on a tricuspid heart valve 18 (FIG. 1B). The introducer catheter assembly 102 can be configured for insertion into a jugular vein 12 over a guide wire (not shown) and advancement from the superior vena cava 14, through the right atrium 16 (FIG. 1B) of a patient's heart 10, and into the inferior vena cava 20.

Referring to FIG. 1B, the visualization catheter assembly 104 can be inserted into and through a lumen of the introducer catheter assembly 102. The needle catheter assembly 106 can be inserted over the guidewire from a femoral incision site 22 through the inferior vena cava 20 and into the lumen of the introducer assembly 102. A first aperture 126 in the shaft 114 of the introducer catheter assembly 102 allows the needle catheter assembly 106 to extend into the right atrium 16 to allow the needle tip (not shown) to penetrate targeted tissue and deploy anchors (not shown) for reducing the heart valve leaflet(s). The visualization catheter assembly 104 can be further extended through a second aperture 128 of the shaft 114 of the introducer catheter assembly 102 into the right atrium 16 to provide visualization of the interior anatomy during a surgical procedure. Accordingly, as will be further discussed in subsequent sections, the introducer catheter assembly 102, the visualization catheter assembly 104, and the needle catheter assembly 106 can together be used as a system 100 to perform the annulus reduction procedure on the tricuspid heart valve 18. Some embodiments of the system 100 provided herein can provide the benefit of enabling a minimally invasive approach to performing an annulus reduction procedure. Some embodiments of the system 100 provided herein present the advantage of quickly performing a medical surgical procedure, for example, completing an annulus reduction procedure in a shorter time frame as compared to the time frame for completing an open heart surgery.

Some embodiments of the system 100 and assemblies 102, 104, 106 provided herein, either alone or in combination, may be configured for use in minimally invasive, interventional cardiology procedures for treating cardiovascular disease. Examples of minimally invasive, interventional cardiology procedures can include, but are not limited to, cardiac procedures such as percutaneous heart valve repair (e.g., tricuspid or mitral valve repair) or replacement, angioplasty, stenting, atherectomy, embolic protection related procedures, and the like. In some cases, the system 100 and the assemblies (e.g., the introducer catheter assembly 102) thereof can be configured for repairing a heart valve, e.g., a tricuspid valve 18 or a mitral valve. In some embodiments, the visualization system 100 and the assemblies 102, 104, 106 can be configured for visualizing and/or repairing other regions of a patient's body, for example, the peripheral regions of the body. Thus, the system 100 and the assemblies thereof can be used for a wide range of medical applications that can benefit from using catheter-based visualization within a blood-field anatomy.

Figures 2A, 2B:
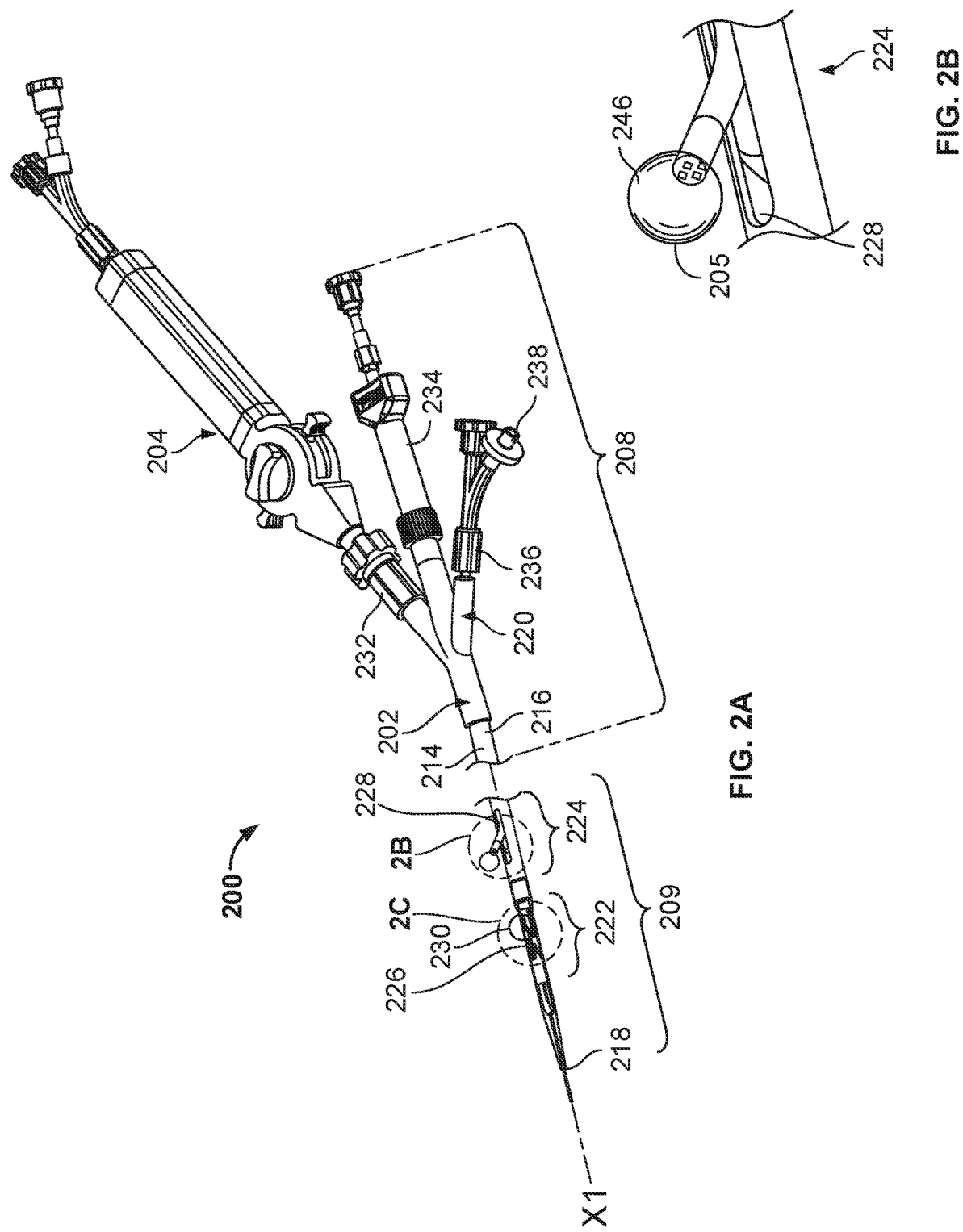
FIGS. 2A-2D are perspective views of an exemplary system provided herein that includes an introducer catheter assembly and a visualization catheter assembly.
Figure 2C:
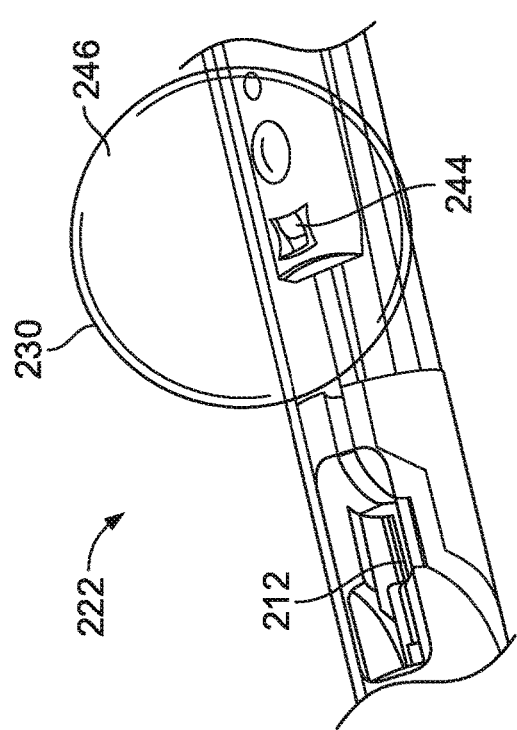

Referring to FIGS. 2A-2C, an exemplary system 200 provided herein includes an introducer catheter assembly 202 and a visualization catheter assembly 204. FIG. 2A shows proximal and distal portions 208, 209 of the introducer catheter assembly 202. FIG. 2B shows a magnified view of a distal portion 209 of the introducer catheter assembly 202, in which a distal tip 205 of a visualization catheter assembly 204 is shown extending therefrom. FIG. 2C shows a magnified view of a distal portion 209 of the introducer catheter assembly 202 configured for introducing a needle catheter assembly 206 (FIG. 2D) into the patient's anatomy. The depicted embodiment of the introducer catheter assembly 202 includes a hub portion 220 coupled to a proximal end 216 of the flexible, elongate shaft 214. The shaft 214 of the introducer catheter assembly 202 can define a lumen extending between the proximal end 216 and a distal end 218. The hub portion 220 and the shaft 214 of the introducer catheter assembly 202 can configured to receive at least a portion of the visualization catheter assembly 204, for example, allowing a distal tip 205 of the visualization catheter assembly 204 to be advanced from the distal portion 209. The distal end 218 of the introducer catheter assembly 202 can be configured to receive at least a portion of a needle catheter assembly 206 (FIG. 2D) such that a distal tip 207 of the needle catheter assembly 206 can be advanced into the right atrium from a femoral vein incision.

Referring to FIG. 2A, the proximal portion 208 of the introducer catheter assembly 202 includes a hub portion 220 that is configured for receiving one or more ancillary devices, for example, the visualization catheter assembly 204. The depicted introducer catheter assembly 202 also includes the elongate shaft 214 coupled to the hub portion 220 and extending distally therefrom. The distal portion 209 of the visualization catheter assembly of FIG. 2A includes various features. As will be discussed in greater detail in further sections, the distal portion 209 can define a first aperture 226 at a first distal portion 222, a second aperture 228 at a second distal portion 224, and a visualization feature 230.

The hub portion 220 of the introducer catheter assembly 202 can include one or more receiving ports. For example, as shown in FIG. 2A, some embodiments of the hub can include three ports: a first port 232, a second port 234, and a third port 236. In some cases, the hub portion 220 of the introducer catheter assembly 202 can include a first port 232 configured for receiving an ancillary device. For instance, the first port can be configured to receive an ancillary device that includes, but is not limited to, a visualization catheter, a surgical catheter, a guide catheter, a guidewire, and combinations thereof. As shown in FIG. 2A, the first port 232 receives the visualization catheter assembly 204 in the system provided herein.

The hub portion 220 can optionally include the second and third ports 234, 236 for receiving second and third ancillary devices, or assemblies. The second and third ports 234, 236 can allow the introducer catheter assembly 202 to receive multiple ancillary devices such that each ancillary device can be independently attached to and/or inserted into the introducer catheter assembly 202.

In some cases, the hub portion 220 can optionally include a venting element 238 (which can also be referred to as a degassing vent) coupled to one or more ports. As shown in FIG. 2A, the venting element 238 is coupled to the third port 236 to release gases (e.g., air) from within the introducer catheter device 302. In some cases, the venting element 238 can be adapted for removing gas, such as air, from within internal cavities of the hub portion 220, while liquids, such as blood, remain within the hub portion 220.

Still referring to FIG. 2A-2C, the distal portion 209 of the introducer catheter assembly 202 includes various features that allow the assembly 202 to be used in conjunction with other devices, such as the visualization catheter assembly 204 and the needle catheter assembly 206. These features can include the first and second apertures 226, 228, which are defined at predetermined locations, e.g., the first and second distal portions 222, 224, along the shaft 214 of the introducer catheter assembly 202. The first and second apertures 226, 228 are configured to allow a first device and a second device respectively received therein to extend out of the shaft 214 of the introducer catheter assembly 202 during a medical procedure.

Referring to FIGS. 2A, C and 2D, the first aperture 226, defined by a portion of the shaft 214 of the introducer catheter assembly 202, can be shaped and sized to allow a first ancillary device, e.g., the needle catheter assembly 206 (FIG. 2D), to extend from of the first distal portion 222 of the shaft 214. In particular, the first aperture 226 can be configured to allow the first ancillary device, which can be received at the distal end 218 of the shaft 214, to exit from the first distal portion 222 of the shaft 214. In some cases, a movable deployment element (e.g., a slidable ramp element 248) can be disposed within the shaft 214 to facilitate the deployment of the first ancillary device from the introducer catheter assembly 202. The deployment element can be configured, in some cases, to allow the first ancillary device to deflect at an angle relative to a longitudinal axis "X1," (see FIG. 2A) defined by the shaft 214 of the introducer catheter assembly 202.

Referring back to FIG. 2D, certain embodiments of the introducer catheter assembly 202 include the movable deployment element, which is a slidable ramp element 248 configured to engage with a portion of the needle catheter assembly 206 proximate to the first aperture 226. The slidable ramp element allows the needle catheter assembly 206 to be directed at an angle relative to the longitudinal axis while the needle catheter assembly 206 is being advanced from the first aperture 226. In some cases, the ramp element 248 can angulate the needle catheter assembly 206 at an angle ranging from 0 degrees to about 90 degrees (e.g., from about 0 degrees to about 10 degrees, from about 0 degrees to about 20 degrees, from about 0 degrees to about 30 degrees, from about 0 degrees to about 40 degrees, from about 0 degrees to about 50 degrees, from about 0 degrees to about 60 degrees, from about 0 degrees to about 70 degrees, from about 0 degrees to about 80 degrees, or from about 0 degrees to about 90 degrees). In some cases, the deployment element can allow the needle catheter assembly 206 to radially angulate between about ±45 degrees relative to a transverse plane orthogonal to the longitudinal axis. The deployment element and structures for allowing angulation of the ramp element 248 will be discussed in greater detail with FIGS. 3C-3E.

Figure 3A:
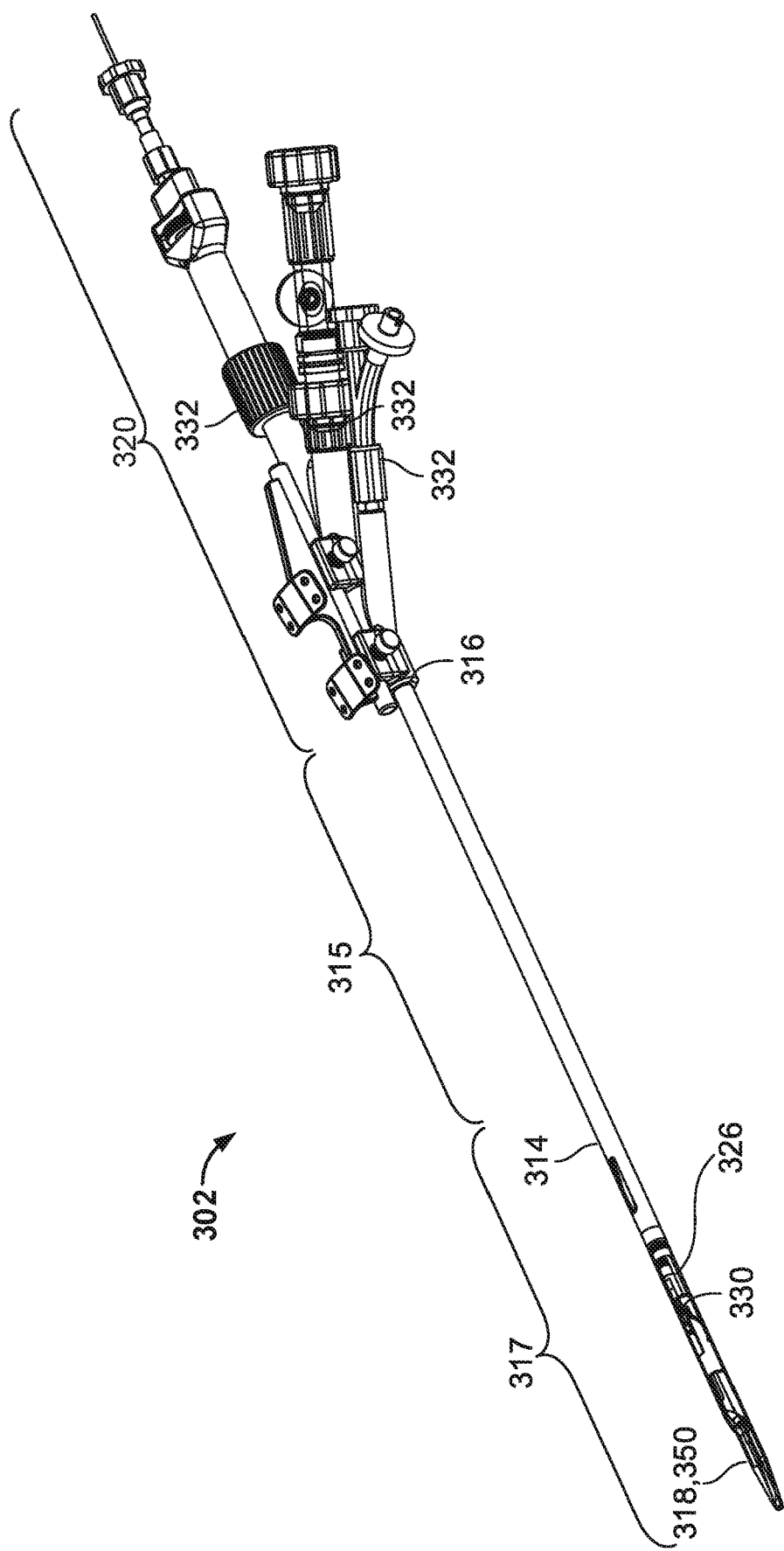
FIGS. 3A-3E are views of an exemplary introducer catheter device provided herein.
Figure 3B:
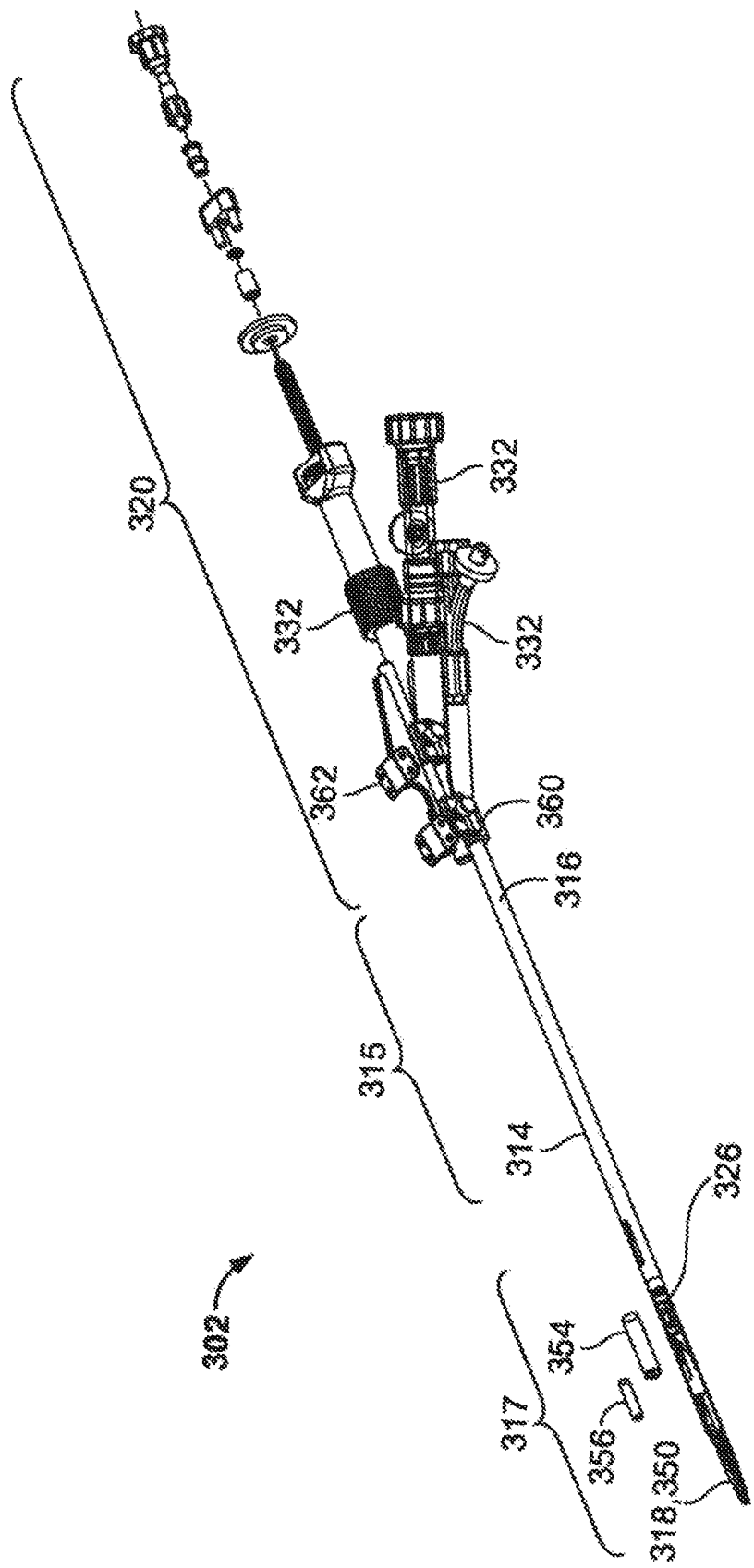
Figure 3C:
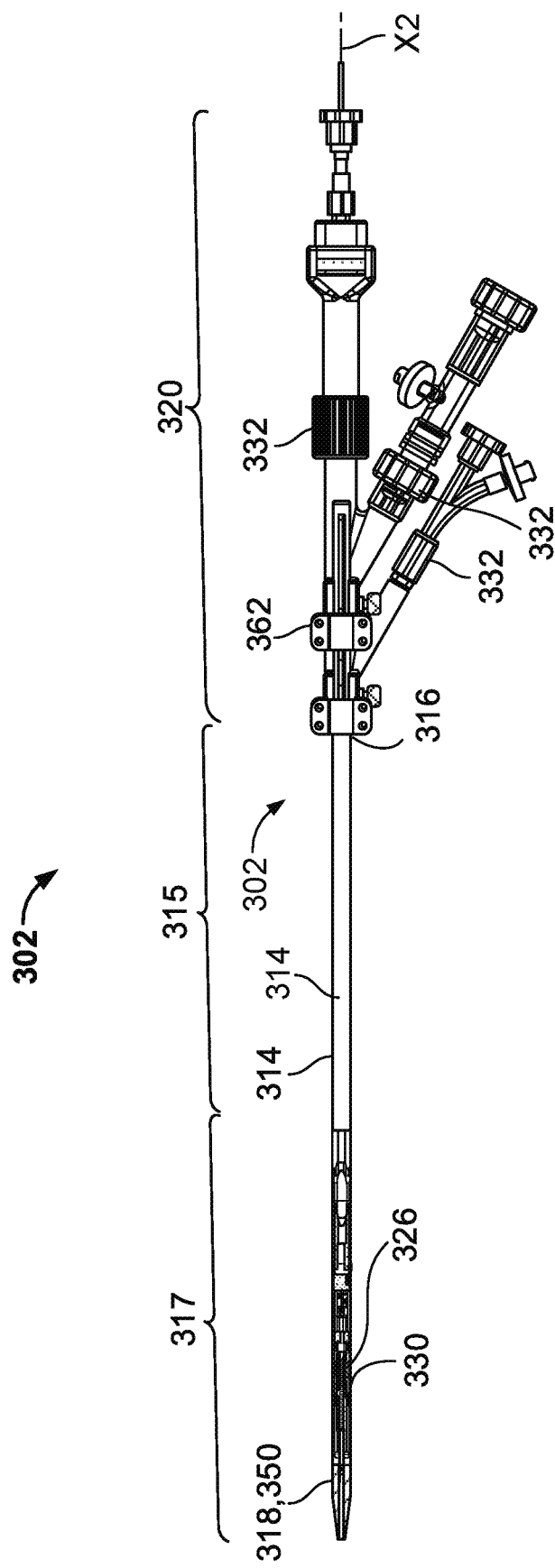

In some cases, the needle catheter assembly 206 may be rotated radially by torqueing the shaft 214 of the introducer catheter assembly 202 such that the needle and the visualization features (e.g., visualization feature 230) of the introducer catheter assembly 202, when rotated together, maintain alignment with respect to one another when a user makes a radial adjustment. Radial adjustments may be achieved by rotating the introducer catheter assembly 202 and the needle catheter assembly 206 (e.g., the system 200) relative to the patient's anatomy. If desired, when the system 200 is in a desired position, the user may secure (e.g., lock, suture or clamp) the system 200 to the patient to maintain the position. In some cases, a bracket 362, as shown in FIGS. 3A-3C, coupled to the needle catheter assembly 206 may be used to secure the system 200 in position. In some cases, the needle catheter assembly 206 may be configured to rotate radially independently of the introducer catheter assembly 202.

In some cases, the first aperture 226 can be defined by one of various polygonal shapes, such as a circular-shaped, an oval-shaped, or a rectangular-shaped opening. In some cases, the first aperture 226 can include a slot-shaped opening. The first aperture 226 can, in some cases, be shaped to allow the first ancillary device to deflect at an angle ranging from 1 degree to about 120 degrees, or from 1 degree to about 180 degrees (e.g., from 0 degree to about 5 degrees, from 5 degrees to about 30 degrees, from 30 degrees to about 60 degrees, from 60 degrees to about 90 degrees, from about 90 degrees to about 120 degrees, or from about 120 degrees to about 180 degrees). The range of angle deflection may adjusted, as desired, to a suitable angle range that ranges between 1 degree and 180 degrees to allow the use of the first ancillary device with the devices and systems 200 provided herein.

Figure 2D:
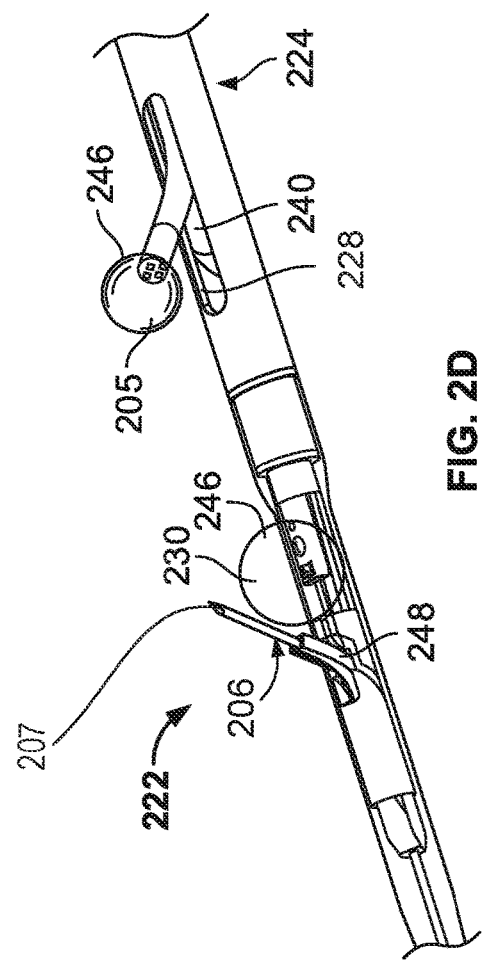

Still referring to FIGS. 2A, 2C and 2D, a second aperture 228 can be defined by a portion of the shaft 214 of the introducer catheter assembly 202, and connected with the lumen of the introducer catheter assembly 202. The second aperture 228 can be configured to allow a second ancillary device, e.g., the visualization catheter 204, received at the hub portion 220 of the assembly 202 and exit from the second distal portion 224. The second aperture 228 can be shaped into one of various polygonal shapes, such as a circular-shaped, an oval-shaped, or a rectangular-shaped aperture. In some cases, the second aperture 228 can include an elongate slot formed longitudinally along the shaft and that preferably includes rounded ends.

Some embodiments of the introducer catheter assembly 202 can optionally include a visualization feature 230 configured for visualizing anatomical regions and devices adjacent to the distal shaft of the introducer catheter assembly. The visualization feature 230 includes a camera 244 (e.g., visible camera), as shown in FIG. 2C, encapsulated within a weeping balloon 246. A weeping balloon can be made of a transparent material, such as silicone, with a plurality of perforations to allow the balloon to "weep." The "weeping" allows saline to clear blood from balloon surfaces that interface with an anatomical surface. The visualization feature 230 can include an ultrasound probe, in some cases. Certain embodiments of the introducer catheter assembly 202 can include a visualization feature 230 configured to provide visualization of anatomical regions and the needle catheter assembly 206 as it exits from the first aperture 226. The visualization feature 230 may include balloons that are shaped and located along the shaft such that various shapes of ancillary tools and the patient's anatomy can be visualized in the blood field during a medical procedure. The visualization feature 230 can be used as a steerable tracking tool to observe the deployment of devices and systems 200 provided herein at desired locations within a patient's anatomy.

Figure 3D:
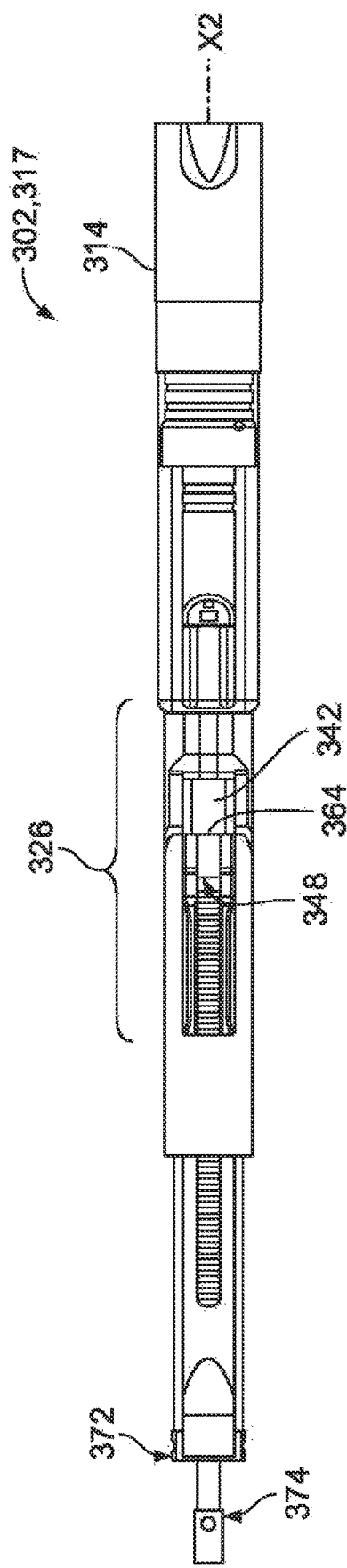
Figure 3E:
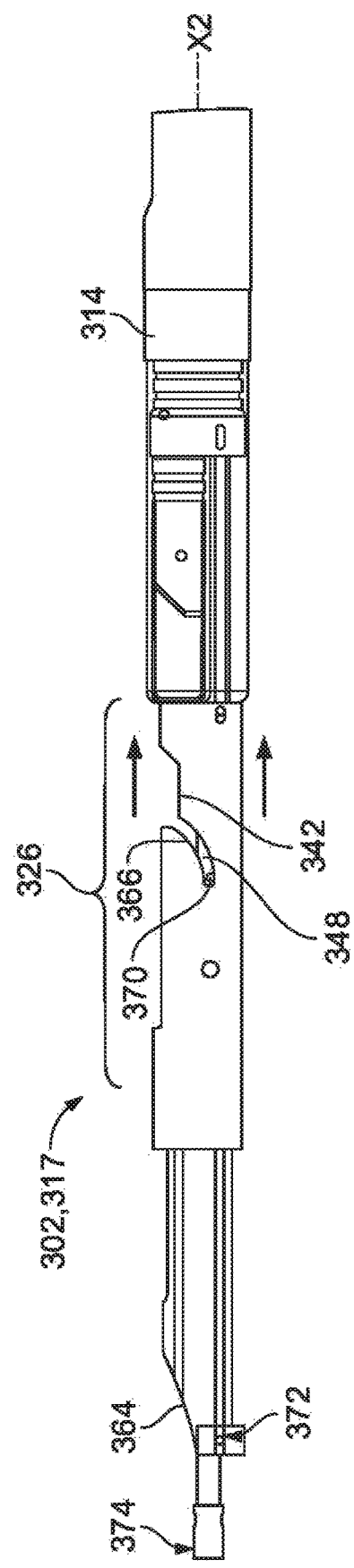

FIGS. 3A-3E are views of an exemplary introducer catheter device 302 provided herein. FIGS. 3A and 3B are perspective views of the device 302 shown in an assembled state and an exploded state, respectively. FIGS. 3C and 3D are plan views of the device 302 showing the entire length of the device 302 and a magnified view of a distal portion of the device 302, respectively. FIG. 3E is a magnified side view of a distal portion of the device 302, respectively.

Referring to FIGS. 3A and 3B, the introducer catheter device 302 includes a hub portion 320 coupled to a shaft portion 314. The shaft portion 314 can include a body that has a proximal portion 315, a proximal end 316 coupled to the hub portion 320, a distal portion 317, and a distal end 318. At least a portion of the shaft portion 314 may be flexible, or semi-flexible. For example, in some cases, the proximal portion 315 and the proximal end 316 of the shaft can be a flexible, tubular component. The distal end 318 can include a flexible atraumatic tip portion 350 for minimizing tissue damage and blood vessel disruption during insertion of the introducer catheter device 302 into a blood vessel, e.g., the jugular vein. The tip portion 350 can include a tapered beveled distal end portion configured to bias the tip portion to a buckled state when subjected to a compressional axial force, which allows the tip portion 350 to easily conform to tortuous contours of a patient's anatomy during device insertion.

The distal portion 317 of the introducer catheter device 302 can include a visualization feature 330 configured for visualizing anatomical regions and devices at, or adjacent to, the distal portion 317 of the shaft 314 of the introducer catheter device 302. The visualization portion 330 can include at least one weeping balloon 354, 356. As shown in FIG. 3B, the device can include a dual-balloon design that includes two weeping balloons, where an outer weeping balloon 354 encapsulates an inner balloon 356. The outer and inner weeping balloons 354, 356 can encapsulate a portion of the shaft 314 containing a visualization element, such as a distal camera (e.g., camera 244 of FIG. 2C). The outer balloon 354 can serve as a compliant balloon for contacting and stabilizing the introducer catheter device 302 when it comes into contact with an anatomical feature, for example, the coronary sinus, an atrial wall, or a leaflet. The inner balloon 356 can facilitate maintaining a constant pressure to stabilize the field of view of the visualization element (e.g., camera). A constant pressure can help to provide reliable visualization to the user since pressure changes within the balloon may affect the focal length of the visualization element, and thus, affect the focusing capabilities of the visualization feature 330. Certain embodiments of the introducer catheter device 302 can include a visualization feature 330 configured to provide visualization of anatomical regions and the needle catheter assembly as it exits from a first aperture 326. In some cases, the visualization feature 330 can also include a lighting element (not shown), such as a LED or an optic fiber, to illuminate the field of view of the visualization element.

Still referring to FIGS. 3A and 3B, a hub portion 320 can allow the introducer to be fluidly connected to ancillary devices (e.g., a needle catheter device, and a visualization catheter device), fluid supply (e.g., saline), actuators (e.g., a micrometer), and/or other components (e.g., a degasser, one or more electrical connection). The hub portion 320 can include a connector body 360 for providing two or more port connections 332 (for example, two three, four, five, or more than five port connections). In some cases, the port connections 332 are coupleable to various fluid-administration adapters and components, such as a Y-connector or a luer fitting. In some cases, the port connections 332 can be coupled to one or more fluid-administration adapters and/or components. In some cases, at least one port 332 connection can coupleable or coupled to a blood-leakage minimizing device insertion hub. In some cases, at least one port connection 332 can be coupleable or coupled to an actuator, or a distance-measuring equipment (e.g., micrometer) configured for advancing or retracting an ancillary device (e.g., a needle catheter device) contained within the lumen of the introducer catheter device. In some cases, at least one port connection 332 can be coupleable or coupled to a degasser for releasing a gas (air) from the hub portion. In some cases, the hub portion 320 can optionally include a bracket 362 for releasably anchoring the introducer catheter device 302 to a location proximate to the patient for minimizing agitation of the device 302 during a medical procedure.

Referring to FIGS. 3C-3E, the introducer assembly device 302 provided herein can include a first aperture 326 configured to allow another device received within a lumen 364 of the device 302 to exit from the distal shaft portion 317 of the introducer 302. As depicted, the introducer assembly device 302 includes a slidable ramp element 348 configured to engage with a needle catheter assembly (e.g., the needle catheter assembly of FIG. 2A-2C). The slidable ramp 348 can advance the needle catheter assembly at an angle relative to a longitudinal axis "X2" defined by the shaft 314 while also advancing the needle catheter assembly in a proximal direction from the aperture 342.

In particular, as shown in FIGS. 3D-3E, the first aperture 326 of the introducer catheter device 302 defines two elongated, curvilinear slots 366 along the shaft 314. The curvilinear slots 366 can be configured to interface with a slidable ramp element 348 such that the ramp element 348 can slide in a distal direction, or a proximal direction, along the longitudinal axis X2. In particular, the ramp element 348 can include a first portion that has two radially-opposed pins 370 configured to insert into and slidably move within the curvilinear slots 366. The ramp element 348 also includes a second portion 372 that can be configured to be hingeably coupled to a rod 374 such that the ramp element 348 can angulate to (also shown by a similar embodiment in FIGS. 3A and 3B) a predetermined angle when advanced in a proximal direction along a pathway defined by the curvilinear slots 366. The ramp element 348 may be advanced in a proximal direction (depicted by the arrows in FIGS. 3D and 3E) or, alternatively, in a distal direction, by an axial force being applied to a rod 374 at the hub portion 320 of the introducer catheter device 302, which can be coupled to the hingable second portion 372 of the ramp element 348.

Various components the introducer assembly device 302 can be made of a polymer, a metal, a ceramic, or a combination thereof. In some cases, components such as the ramp element 348 can be made of a metallic material, such as nitinol, stainless steel, a titanium alloy, a platinum alloy, and combinations thereof. In some cases, components such as the shaft 314 can be made of one or more polymeric materials, such as silicone, polyurethane, peek, polyamide, pebax, nylon, and combinations thereof. Various components of the introducer assembly device 302 can be assembled together by manufacturing processes that includes, but are not limited, soldering, laser welding, adhesive bonding, press-fitting, extrusion, tube drawing, and combinations thereof.

Figure 4C:
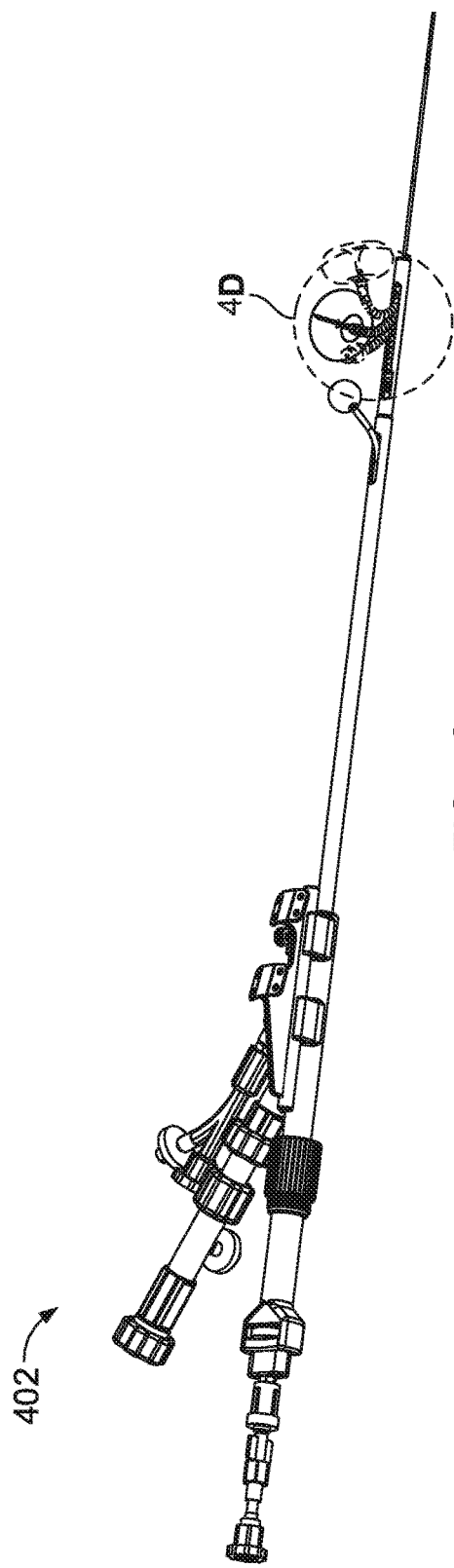
Figure 4D:
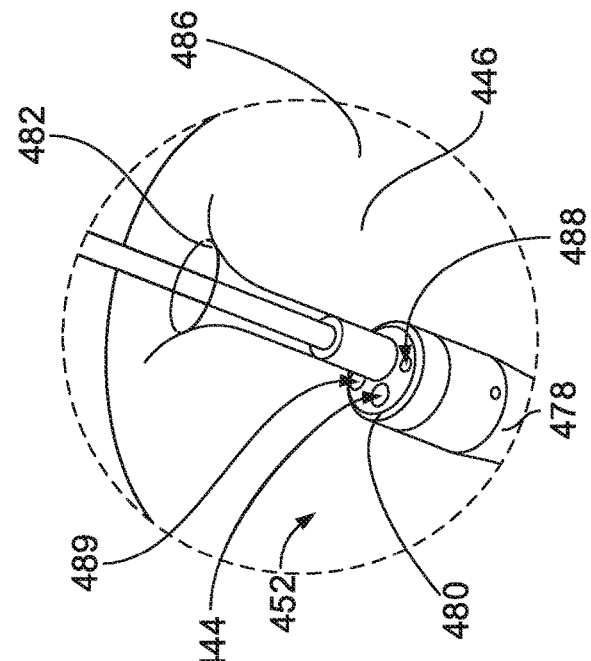
Figure 4E:
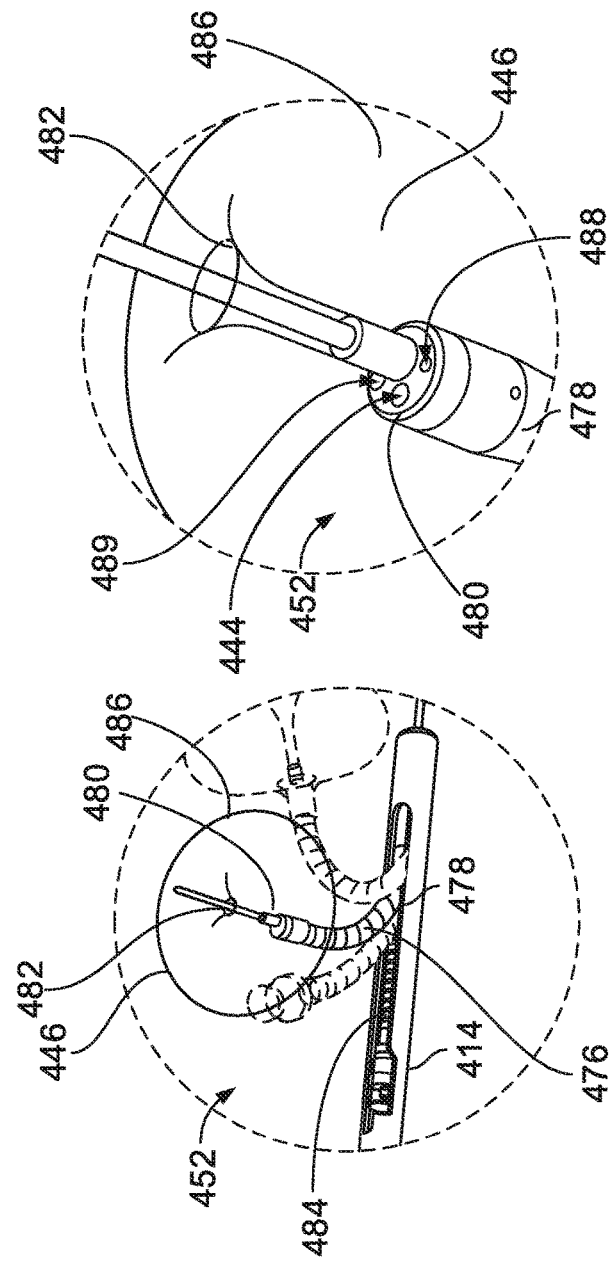

FIGS. 4A-4E are views of another exemplary introducer catheter device 402 provided herein. FIGS. 4A and 4C are perspective views of the device 402 and FIG. 4B is a side view of the device 402. FIGS. 4D and 4E are magnified views of a distal portion 409 of the device 402. The embodiment of the device 402 provided in FIGS. 4A-4E includes a proximal portion 407 having similar components as compared to the embodiment of FIGS. 3A-3E. As such, the discussion of this embodiment will be primarily focused on a distal portion 409 of the introducer catheter device 402.

Referring to FIGS. 4A-4C, the introducer catheter device 402 includes a hub portion 420 coupled to a shaft 414. The shaft 414 can include a body that has a proximal portion 415, a proximal end 416 coupled to the hub portion 420, a distal portion 417, and a distal end 418. At least a portion of the shaft 414 may be flexible, or semi-flexible. For example, in some cases, the proximal portion 415 and the proximal end 416 of the shaft 414 can be a flexible, tubular component. The distal end 418 can include a flexible atraumatic tip 450.

The distal portion 417 of the introducer catheter device 402 can include a visualization feature 452 configured for visualizing anatomical regions and devices adjacent to the distal portion 417 of the introducer catheter device 402. The visualization feature 452 can be configured to provide visualization of anatomical regions and allow passage of a needle catheter assembly. In some cases, the visualization feature 452 may be disposed on an articulating body 476 that includes a proximal end 478 and a distal end 480, and defines a lumen 482 therethrough the articulating body 476. The lumen 482 of the articulating body 476 can be configured to receive a portion of an ancillary device, such as the needle catheter assembly, as shown in FIGS. 4D and 4E. When in a non-deflected state, the articulating body 476 may be seated in a cavity 484 within the shaft 414 to minimize the profile of the distal portion 417 of the shaft 414 during device delivery. When in a deflected state, the articulating body 476 may be positioned, as desired, to view surrounding anatomical features, or introduce the needle catheter assembly. The visualization feature 452 can include a visualization element 444 (e.g., visual camera) encapsulated within a weeping balloon 446 at the distal end 480 of the articulating body 476.

As shown by the dotted line depictions in FIGS. 4A-4D, the articulating body 476 of the introducer catheter device 402 may be deflected to various angles relative to a longitudinal axis "X3" (FIG. 4B) defined by the shaft 414 of the introducer catheter device 402. The articulating body 476 of the visualization feature 452 can be configured to deflect, as desired, the distal end 480 of the visualization feature 452 in a radially outward direction from the shaft 414 of the introducer catheter device 402. The articulating body 476 can be configured for single plane deflection (deflects along an X axis "X3" in one direction only) or bi-plane deflection (deflects along an X axis and a Y axis). For example, in some cases, as shown in FIG. 4A, the articulating body 476 can be configured for bi-plane deflection, and therefore may deflect along the longitudinal axis ("X3" axis, or also referred to as on-plane). In some cases, the articulating body 476 can also deflect along a transverse plane ("Y3" axis, or also referred to as off-plane), which is orthogonal to the longitudinal axis "X3". The articulating body 476 may deflect to various curve angles along the longitudinal axis X3, and optionally along the transverse plane. In some cases, the articulating body 476 may be configured to have a curve angle that ranges from about 1 degree to about 180 degrees, or from 1 degree to about 270 degrees. In some cases, the bending angle of the articulating body 476 can exceed 270 degrees.

In some cases, the articulating body 476 can include a tubular body. In some cases, the articulating body 476 can include, but is not limited to, a braided shaft, a perforated hypotube (e.g., a slotted hypotube), a coiled spring, a polymer tube (e.g., a corrugated tube), and combinations thereof. The articulating body 476 may be composed of a metal, a polymer, a ceramic material, or combinations thereof.

In some cases, the articulating body 476 of the introducer catheter device 402 can be achieve a bend radii that is less than 2 centimeters. In some cases, a larger bend radius (e.g., greater than 2 centimeters) can be achieved by disposing (e.g., coating) a polymer tubing over the articulating body 476 to create a corrugated outer profile that allows for a flexed working channel.

As shown in FIGS. 4A-4E, the visualization feature 452 of the introducer catheter device 402 can include at least one balloon 486 (e.g., a weeping balloon) disposed at the distal end of the articulating body 476. In some cases, the balloon 486 can include a dual-balloon design provided herein. As shown best in FIG. 4D, the balloon 486, when deployed, can form a donut-shaped balloon such that an ancillary device or component can pass through a center region of the balloon without penetrating through the wall of the balloon. The balloon 486 may be deployed by inflating the balloon with a fluid, e.g., saline, supplied by a port 488 at the distal end 480 of the articulating body 476. The port 488 can be connected to a lumen (not shown) that provides a fluid pathway between the distal end 480 of the articulating body 476 and the hub portion 420 of the introducer catheter device 402. In some cases, the balloon 486 can include various other shapes, such as a spherical balloon, in which the ancillary device or component penetrates through the wall of the balloon.

Still referring to FIG. 4E, the introducer catheter device 402 can include a visualization element 444 disposed at the distal end 480 of the articulating body 476. The visualization element 444 can include, but is not limited to, a digital camera, or an ultrasound sensor. As shown in the depicted embodiment, the visualization element 444 is located on a distal face of the distal end of the articulating body 476 to facilitate an axially-directed field of view. In some cases, the introducer catheter device 402 can include multiple visualization elements 444. In some cases, one or more of the multiple visualization elements 444 can be radially-directed, axially-directed, or a combination thereof. The visualization feature 452 can optionally include, in some embodiments, a lighting element 489, such as a LED or an optic fiber, to illuminate the field of view of the visualization element 444.

Figure 5C:
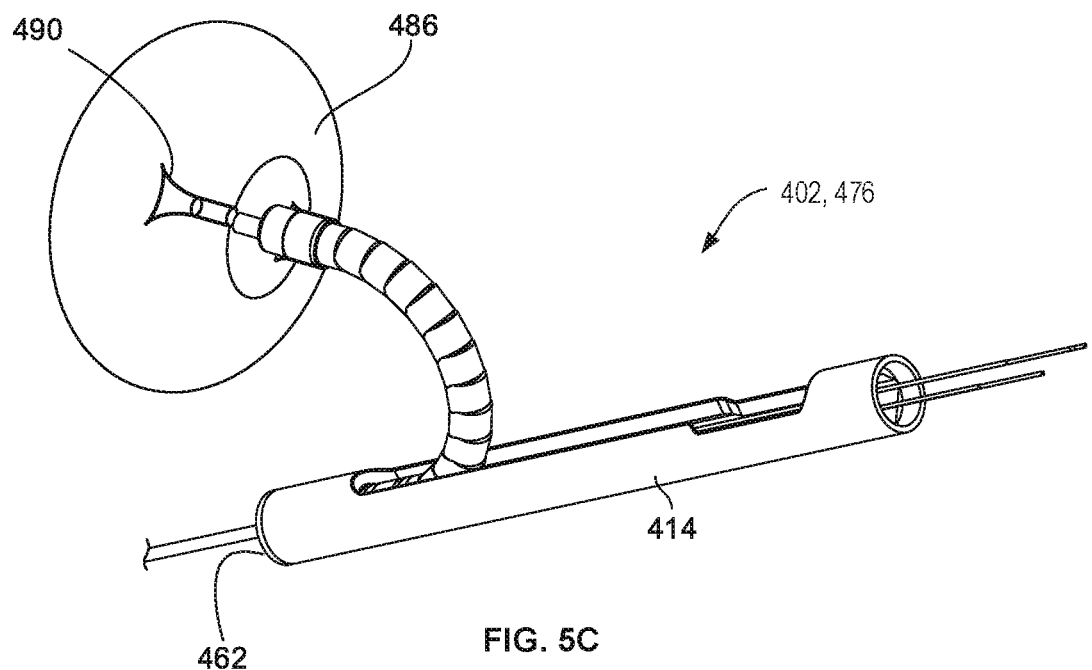
Figure 5D:
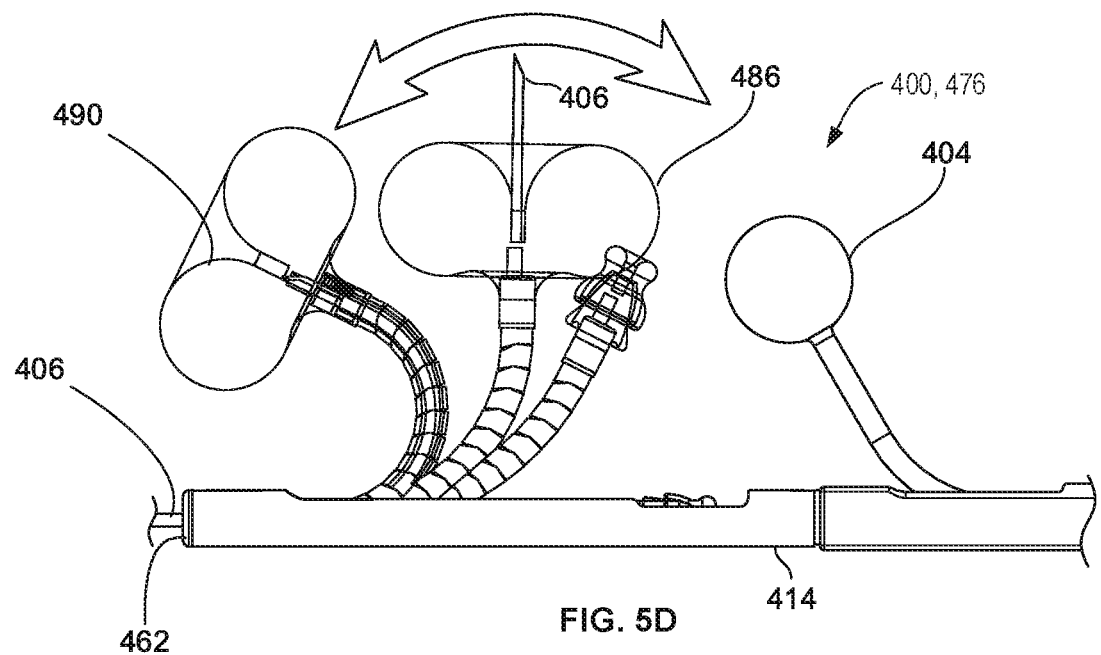

FIGS. 5A-5D are a series of illustrations showing how the distal portion 409 of the introducer catheter device 402 of FIGS. 4A-4E can be actuated as a system 400 during a medical procedure. The system 400, as shown in FIG. 5D, may include the introducer catheter device 402, the needle catheter device 406, and the visualization catheter device 404. For simplicity purposes, select portions of the introducer catheter device 402 are shown in FIGS. 5A-5D.

Referring to FIG. 5A, the introducer catheter device 402 is guided over a placed guidewire 403 to a desired target location within a patient's anatomy. During an annulus reduction procedure, the introducer catheter device 402 can placed such that the distal portion 409 of the introducer catheter device 402 is positioned within the right atrium of the heart. The needle catheter device 406 is advanced over the guidewire towards the distal end of introducer catheter device. In some cases, the needle catheter device 406 is introduced through an incision of the femoral vein and advanced from the femoral vein to the inferior vena cave until the needle catheter device 406 enters the right atrium.

Referring to FIG. 5B, the needle catheter device 406 is received into a lumen 462 at the distal end 418 of the introducer catheter device. Once the needle catheter device 406 is placed into the articulating body 476 of the introducer catheter device, the articulating body 476 can be deflected by pulling lift one or more cables (e.g., two, three, or more than three cables) within the shaft of the introducer catheter device 402 from the hub portion 420 of the introducer catheter device. In particular, a set of cables or rods, shown in FIG. 5D, can be actuated (e.g., pulled proximally) by an actuator (not shown) at the hub portion 420. The cables may be disposed within the articulating body 476 along the one side of the body to bias bending of the distal end 480 of the articulating body 476 away from the shaft 414 of the introducer catheter device 402. The level of deflection when the articulating body 476 bends may depend on the magnitude of the axial force applied to the cables.

Referring to FIG. 5C, the weeping balloon of the introducer catheter device 402 may be deployed, as desired, by a practitioner during the medical procedure.

Referring to FIG. 5D, the introducer catheter device 402 can be deflected to varying degrees (as depicted by the arrow in the figure) to position the needle catheter device 406, as desired, to penetrate the needle at the proper target site within the patient's body. For example, during an annulus reduction procedure on a tricuspid heart valve, the weeping balloon 486 may be positioned against the coronary sinus within a right atrium. Once the weeping balloon 486 is positioned at the target site, the needle catheter device 406 can be passed through an annular bore 490 of the balloon 486.

Figure 6A:
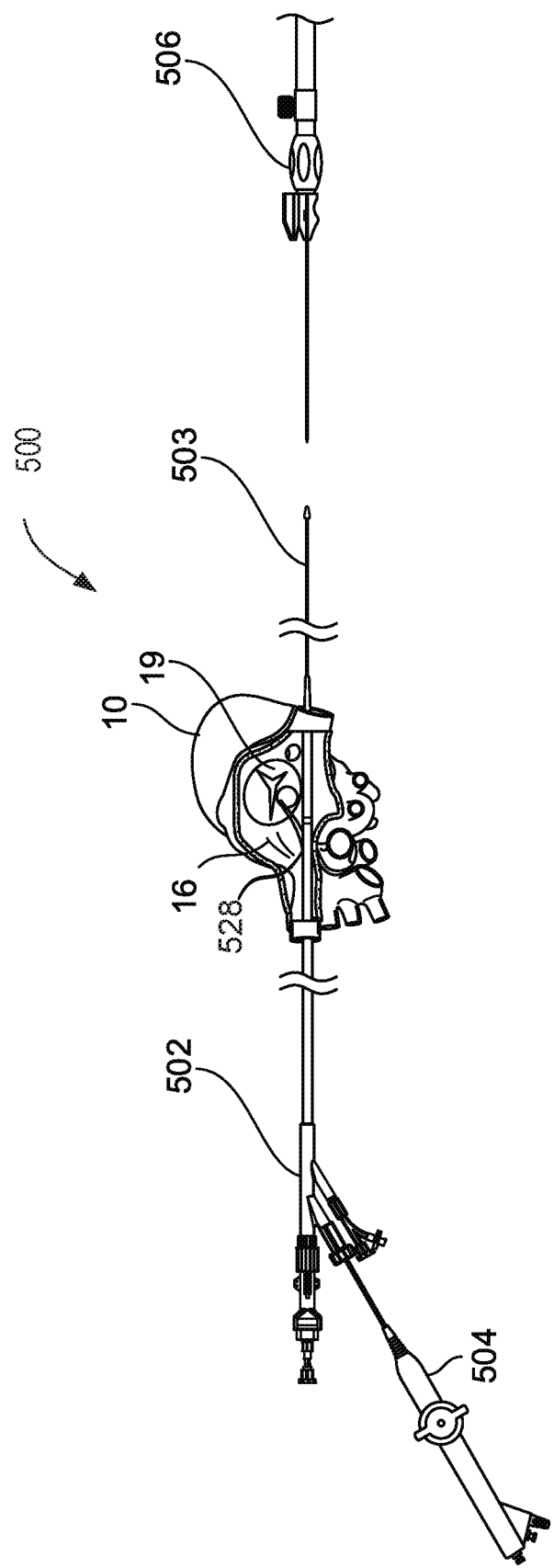
FIGS. 6A-6E are a series of illustrations showing a method of performing a tricuspid annulus reduction procedure using an exemplary system provided herein.

FIGS. 6A-6E are a series of illustrations showing various stages of a method of performing an annulus reduction procedure using an exemplary system 500 provided herein. Referring to FIG. 6A, an exemplary system 500 for performing an annulus reduction procedure includes an introducer catheter assembly 502, a needle catheter assembly 506, and a visualization catheter assembly 504. The visualization catheter assembly 504 can be inserted into the introducer catheter assembly 502 prior, or after the insertion of the introducer catheter assembly 502 into a patient. The visualization catheter assembly 504 and the introducer catheter assembly 502 may be inserted into a jugular vein and the needle catheter assembly 506 may be inserted into a femoral vein of the patient.

The introducer catheter assembly 502 can be advanced from the jugular vein incision site to the superior vena cava and to the right atrium 16 of the heart 10. The needle catheter assembly 506, which is pre-loaded with anchors, is advanced through the femoral vein to the inferior vena cava over the guide wire 503 until it reaches the entrance of the right atrium 16.

Still referring to FIG. 6A, the visualization catheter assembly 504 can be inserted into and advanced through the introducer catheter assembly 502. The visualization catheter assembly 504 can be advanced until it exits through the first aperture 526 of the introducer catheter assembly 502 such that the distal end 505 of the visualization catheter assembly 504 can be positioned within the right atrium 16.

Figure 6B:
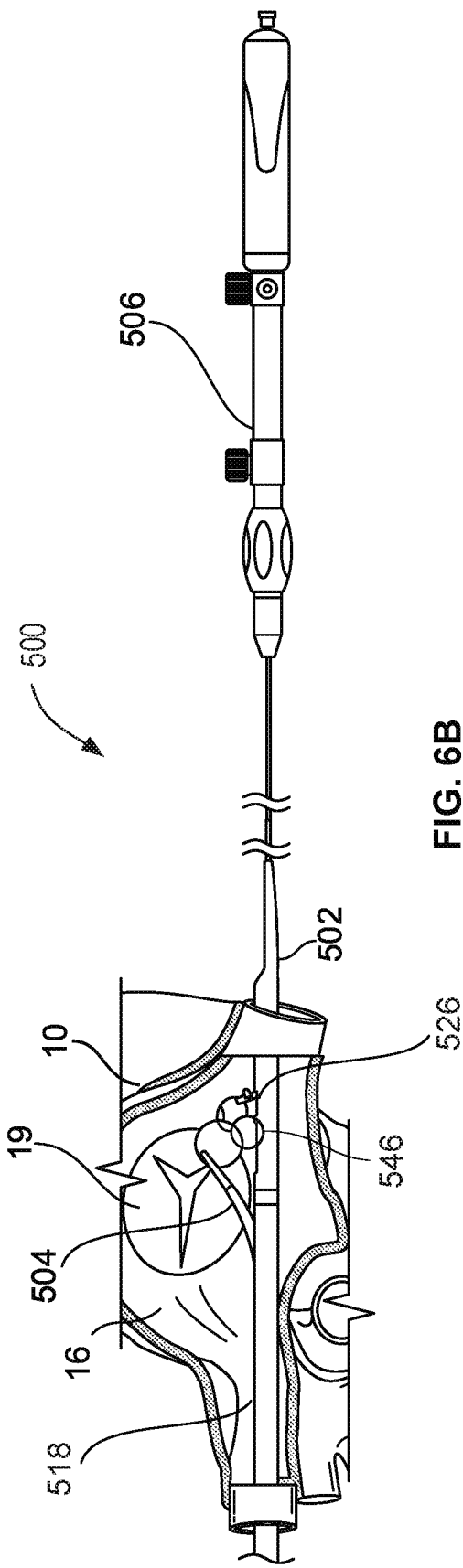

Referring to FIG. 6B, a balloon of the steerable visualization catheter assembly 504 is inflated with inflation media (e.g., saline solution) within the right atrium 16 to provide the user with visualization of the tricuspid leaflet 19. As shown, a visualization balloon 546 of the introducer catheter assembly 502 may be inflated with the inflation media at or adjacent to the first aperture of its distal portion 509. In some embodiments, the visualization balloon 546 can be located at any location along the shaft 518 of the introducer catheter assembly 502, e.g., next to the balloon of the steerable visualization catheter assembly 504 at the coronary sinus location. The two balloons can be used together to provide anatomical visualization within the right atrium 16 during the surgical procedure to assist with positioning a surgical tool, e.g., the needle catheter assembly 506.

Figure 6C:
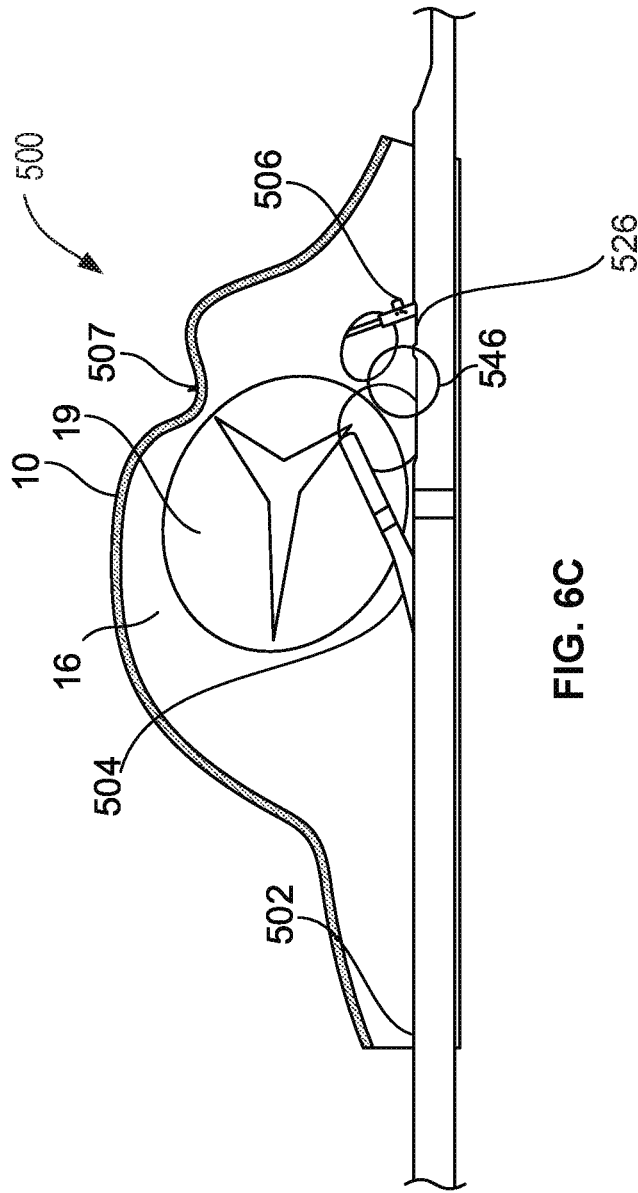

Referring to FIG. 6C, the needle catheter assembly 506 can be advanced through the targeted tissue, e.g., the coronary sinus. The needle catheter assembly 506 can optionally emit a light at the needle tip such that the steerable visualization catheter assembly 504 can visually assess the needle penetration by detection of the emitted light.

Figure 6D:
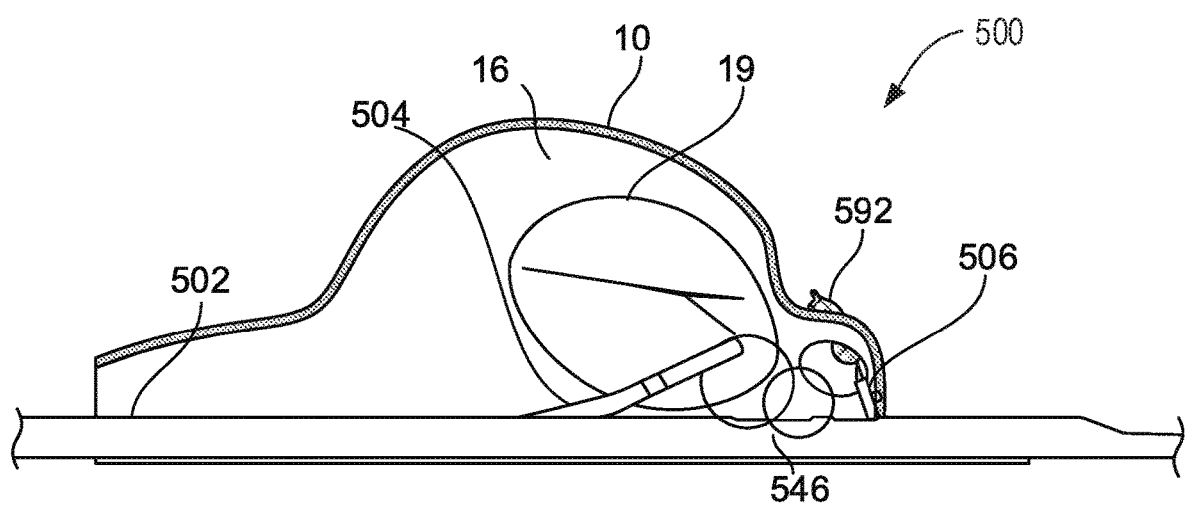

Referring to FIG. 6D, at least one tissue anchor 592 can be delivered through the lumen of a needle 507 of the needle catheter assembly 506 and be deployed into the tissue once the needle 507 has penetrated fully, which can also be described as "tunneled," through the targeted tissue.

Figure 6E:
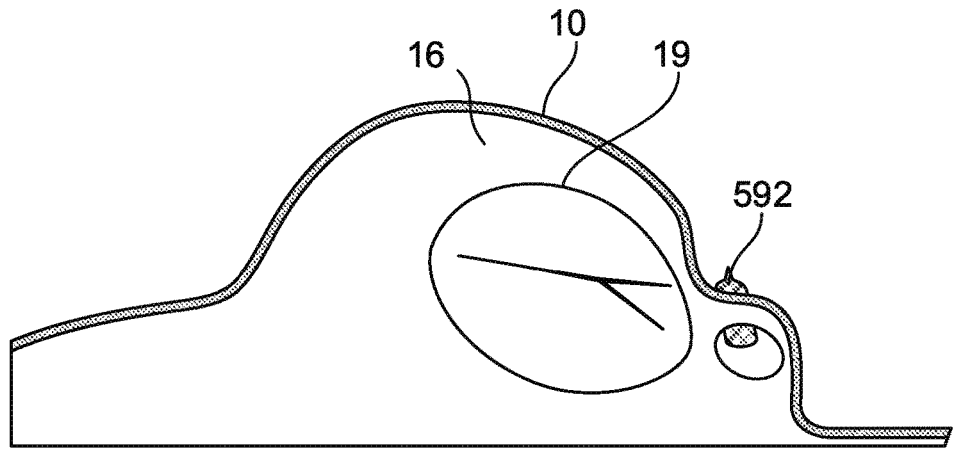

Referring to FIG. 6E, once the targeted tissue has been reduced by the tissue anchor(s) 592, the system 500 can be removed from the patient's body.

It should be understood that one or more design features of the devices provided herein can be combined with other features of other devices provided herein. In effect, hybrid designs that combine various features from two or more of the device designs provided herein can be created, and are within the scope of this disclosure.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

In addition to being directed to the teachings described above and claimed below, devices and/or methods having different combinations of the features described above and claimed below are contemplated. As such, the description is also directed to other devices and/or methods having any other possible combination of the dependent features claimed below.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein. All references, publications, and patents referred to herein, including the figures and drawings included therewith, are incorporated by reference in their entirety.

We claim:

1. An introducer catheter device comprising:
    a handle; and
    an elongate shaft coupled to the handle and extending therefrom, the shaft defining a lumen therethrough and a longitudinal axis, the shaft defining a first aperture in connection with the lumen, and comprising a movable deployment element configured for deploying an ancillary device from the first aperture at an angle relative to the longitudinal axis;
    wherein the shaft comprises a weeping balloon encapsulating a shaft portion comprising a digital camera.

2. The introducer catheter device of claim 1, wherein the deployment element comprises a slidable member and a rail member, the slidable member configured to slidably move along the rail member such that as the slidable member advances in a longitudinal direction either proximally or distally relative to the rail member, the slidable member articulates to a predetermined angle.

3. The introducer catheter device of claim 2, wherein the predetermined angle of the slidable member ranges from about 1 degree to about 180 degrees.

4. The introducer catheter device of claim 2, wherein the deployment element when in a fully deployed state, is positioned at an angle ranging from about 60 degrees to about 80 degrees relative to a longitudinal axis defined by the shaft.

5. The introducer catheter device of claim 2, wherein the deployment element is configured to actuate into a fully deployed state when the slidable member is advanced a predetermined distance in the longitudinal direction proximal to the rail member.

6. The introducer catheter device of claim 5, wherein the predetermined distance ranges from about 5 mm to about 10 mm.

7. The introducer catheter device of claim 2, wherein the slidable member comprises a distal face defining an opening, the opening being sized to engage with a portion of the ancillary device received therein.

8. The introducer catheter device of claim 1, wherein the deployment element comprises a deflectable shaft fully disposed within a cavity defined within the shaft when in a first configuration, and at least partially deflectable in a radially outward direction relative to the cavity in a second configuration.

9. The introducer catheter device of claim 8, further comprising an actuator coupled to the handle, and a cable coupled to and extending from the actuator to the deflectable shaft, wherein the actuator is configured to apply tension to the cable to deflect the deflectable shaft into the second configuration.

10. The introducer catheter device of claim 8, wherein the deflectable shaft deflects to a curve angle that ranges from about 45 degrees to about 180 degrees, or from about 30 degrees to about 270 degrees.

11. A system comprising:
    the introducer catheter device of claim 1; and
    a needle catheter device that includes a proximal end, a distal end, and an elongate shaft, the distal end comprising a needle tip, and the shaft of the needle catheter device configured for being received within the lumen of the introducer catheter device, the needle catheter device being extendable through the first aperture.

12. The introducer catheter device of claim 1, wherein the shaft defines a second aperture in connection with the lumen, the second aperture comprising an elongate slot formed longitudinally along the shaft.

\* \* \* \* \*